(12) United States Patent
Heymans et al.

(10) Patent No.: US 10,457,931 B2
(45) Date of Patent: Oct. 29, 2019

(54) PURIFICATION OF NUCLEIC ACID FROM A SAMPLE CONTAINING NUCLEIC ACID AND ENDOTOXIN

(71) Applicant: AXAGARIUS GMBH & CO. KG, Düren (DE)

(72) Inventors: Stefan Heymans, Solingen (DE); Thorsten Rosenbaum, Jülich (DE)

(73) Assignee: AXAGARIUS GMBH & CO. KG, Düren (DE)

( * ) Notice: Subject to any disclaimer, the term of this patent is extended or adjusted under 35 U.S.C. 154(b) by 191 days.

(21) Appl. No.: 15/477,671

(22) Filed: Apr. 3, 2017

(65) Prior Publication Data
US 2017/0292122 A1    Oct. 12, 2017

(30) Foreign Application Priority Data
Apr. 6, 2016 (DE) .......... 10 2016 106 271

(51) Int. Cl.
*C12N 15/10* (2006.01)

(52) U.S. Cl.
CPC ..... *C12N 15/1003* (2013.01); *C12N 15/1006* (2013.01)

(58) Field of Classification Search
CPC ............ C12N 15/1003; C12N 15/1006; C12Q 2527/125; C12Q 2527/137
See application file for complete search history.

(56) References Cited

U.S. PATENT DOCUMENTS

| | | | |
|---|---|---|---|
| 5,792,651 A | 8/1998 | Colpan et al. | |
| 6,235,892 B1* | 5/2001 | Demmer ............ | C12N 15/1017 536/25.4 |
| 6,699,386 B2 | 3/2004 | Todokoro et al. | |
| 7,179,908 B2* | 2/2007 | Kim ..................... | C07D 487/08 540/460 |
| 7,479,254 B2* | 1/2009 | Kim .................. | B01D 15/3804 422/400 |
| 7,714,111 B2 | 5/2010 | Sun et al. | |
| 7,718,128 B2* | 5/2010 | Kim .................. | B01D 15/3804 422/400 |
| 7,718,371 B2* | 5/2010 | Yoo ................... | B01J 20/28009 422/534 |
| 7,838,036 B2* | 11/2010 | Yoo .................... | B01J 20/28009 424/489 |
| 8,765,393 B2* | 7/2014 | Burton .................. | A61L 2/0011 435/174 |
| 8,816,063 B2* | 8/2014 | Petzel ................ | C12N 15/1006 536/25.4 |
| 9,458,452 B2* | 10/2016 | Singer ..................... | B01D 15/34 |
| 9,663,779 B2* | 5/2017 | Fabis ................... | C12N 15/101 |
| 2010/0326827 A1* | 12/2010 | Lin .................. | G01N 27/44756 204/461 |
| 2018/0169255 A1* | 6/2018 | Gao ........................ | C07K 16/30 |

FOREIGN PATENT DOCUMENTS

| | | |
|---|---|---|
| CN | 103173438 A | 6/2013 |
| EP | 0407037 B1 | 9/1994 |
| WO | WO-9521178 A1 | 8/1995 |
| WO | WO-99063076 A1 | 12/1999 |
| WO | WO-2005003152 A1 | 1/2005 |
| WO | WO-2005111059 A2 | 11/2005 |
| WO | WO-2007115046 A1 | 10/2007 |
| WO | WO-2008104811 A1 | 9/2008 |

OTHER PUBLICATIONS

Ma et al., "Removing Endotoxin From Plasmid Samples by Triton X-114 Isothermal Extraction", *Analytical Biochemistry*, vol. 424, pp. 124-126 (2012).

* cited by examiner

*Primary Examiner* — Lawrence E Crane
(74) *Attorney, Agent, or Firm* — Drinker Biddle & Reath LLP (57) ABSTRACT

Disclosed is a process for purifying nucleic acids, especially plasmid DNA, from a nucleic acid-containing, biologic sample, consisting of (a) preparation of a fluid sample containing nucleic acid and endotoxin each in dissolved form; (b) precipitation at least of nucleic acid and endotoxin from the fluid sample; (c) washing of the components of the fluid sample precipitated out in step b) in order to at least partially remove the endotoxin with at least one washing solution, which contains at least one amine compound with at least two carbon atoms and with a molar mass of ≤500 g/mol and; at least one organic solvent different from the aforementioned amine compound and has a pH-value (20° C.) in the range from pH 3.0 to pH 8.5, and; (d) dissolution of the remaining nucleic acid from the washed, precipitated constituents from step c) using a dissolving buffer and collection of the dissolved nucleic acids in a separate receptacle. The process is suitable for the effective and economical removal of endotoxins.

12 Claims, 1 Drawing Sheet

PURIFICATION OF NUCLEIC ACID FROM A SAMPLE CONTAINING NUCLEIC ACID AND ENDOTOXIN

CROSS-REFERENCE TO RELATED APPLICATIONS

This application claims priority to German Application No. 102016106271.5, filed Apr. 6, 2016, which is incorporated herein by reference in its entirety.

The present invention relates to a process for purifying nucleic acids, particularly plasmid DNA, from a sample, which contains endotoxin in addition to nucleic acid.

Endotoxins are lipopolysaccharides (LPS) and are a constituent of the cell wall of gram negative bacteria such as *Escherichia coli*, for example. The latter bacterium is very commonly used in biotechnological processes, and so endotoxins are frequently present as contaminants in many biotechnology products. In gene therapy and in the manufacture of pharmaceuticals, endotoxins can provoke excessive immune reactions in the living organism (in vivo) with potentially fatal results. Endotoxins have also been shown to have a negative effect upon transfection of nucleic acids in cell cultures (in vitro).

The removal of endotoxins from preparations of biotechnologically generated biologic macromolecules is a recognized problem in the literature. In many processes for purifying DNA, endotoxins are also separated, and they are a frequent contaminant of plasmid separation. Methods employed for purifying DNA are generally chromatographic procedures such as ion exchange and affinity chromatography or an extraction with detergents, of which the most prominent use Triton® X-114 (i.e. 1,1,3,3-tetramethylbutyl) phenyl-polyethylene glycol) and salts of deoxycholic acid. In the article WO 2007/115046 A1 an additional process is described in which the endotoxins which are to be removed are enzymatically broken down.

These state of the art processes have disadvantages, since they are difficult and expensive and require multiple working steps. The disadvantage of ion exchange or affinity chromatography as a purification method is that the preparation of the eluate requires the eluted DNA to be laboriously de-salted, concentrated and extracted from the elution agent before it can be made available for subsequent processing or analyses. Furthermore, the production costs of chromatography solid phases are high, making ion exchange chromatography uneconomical.

In addition, it is known from the literature that complete removal of the endotoxins for an in vitro transfection is not obligatory and only applies to sensitive cell lines. Thus far, there is a need for a cost effective, simple and rapid method to extensively remove endotoxins.

BACKGROUND OF THE INVENTION

Few publications describe a method for removing endotoxins by precipitation with alcohols, since endotoxins and DNA behave very similarly. Using currently established techniques, alcohols such as ethanol and isopropanol cause DNA and endotoxins to precipitate out together.

In the process described in WO95/21178A1 isopropanol is substituted for ethanol as the fluid phase in anion exchange chromatography. Substitution of the univalent alcohol ethanol with the similarly univalent alcohol isopropanol leads to an improved transfection efficiency.

WO 99/063076 A1 describes the removal of endotoxins using ethanol as the fluid phase in anion exchange chromatography. In addition, it describes the use of Triton® X-114, which is known to be well-suited to the removal of endotoxins in this application.

EP 0 407037B1 describes a purification process that encompasses a complicated and onerous fractionated separation with ethanol. Deoxycholate is additionally used as a frequently described and recognized detergent for the removal of endotoxin. The process described is said to separate endotoxins from bacterial polysaccharides, but nucleic acid purification is neither the goal nor the theme of this process.

According to WO2005/003152A1, protein complexes can be separated from endotoxins after binding to a chromatographic surface by means of alkane diols. This process does not function to purify plasmid DNA since it requires a cation exchanger. This limitation applies generally to the direct utility of ion exchange eluates.

The use of basic compounds as helpers for chromatographic purification is recognized in the literature.

U.S. Pat. No. 6,699,386 B2 describes the use of a basic material in the affinity chromatographic separation of endotoxins, wherein the basic material is present bound to a solid surface.

The production of the corresponding purification column is laborious and requires additional purification steps to separate the eluted, endotoxin-free substances. In addition, the capacity of an affinity chromatographic column is limited and dependent upon the quantity of material used, which unnecessarily increases the dead volume and thereby the eluate volume.

U.S. Pat. No. 7,714,111 B2 describes the use of a washing buffer containing an arginine derivative to remove impurities. The process presented in the article is proposed for purification of a monoclonal antibody, which is bound by its Fc-portion to a protein-A affinity chromatography column. A heterologous group of substances can be separated by the aforementioned antibody. This includes both endotoxins and nucleic acids. This process can therefore not be used for the purification of nucleic acids.

From WO 2005/111059 A2, a process for the separation of endotoxins from samples containing plasmid-DNA is disclosed, which utilizes a carbohydrate-based non-ionic detergent together with a silica carrier material. In this process, it can be viewed as a disadvantage that use of the common silica membrane as a carrier material can lead to blockage, particularly when larger quantities of nucleic acids are to be separated. In addition, the yields of nucleic acids are not always satisfactory and the separation performance is equally unsatisfactory for endotoxins.

BRIEF SUMMARY OF THE INVENTION

The goal of the current invention was to advance from the current state of the art to a more economical and simpler process to prepare nucleic acids, particularly plasmid DNA, from a sample containing nucleic acids and endotoxin. In particular, the process should avoid the additional processing steps required in ion exchange chromatography and lead to a reduced investment of time and resources in the preparation of a solution of nucleic acids with reduced endotoxin content. Further, the new process for endotoxin removal should be simple to integrate into existing kits for nucleic acid purification.

The task is resolved by a process for separating nucleic acids, particularly plasmid DNA, from a nucleic acid-containing biologic sample encompassing the following steps:

a) Preparation of a fluid sample containing nucleic acid and endotoxin each in dissolved form;
b) Precipitation of at least nucleic acid and endotoxin from the fluid sample;
c) Washing of the precipitated constituents of the fluid sample removed in step b) in order to at least partially separate the endotoxin with at least one washing solution which contains
   (i) at least one amine compound with at least two carbon atoms and with a molar mass of 500 g/mol and;
   (ii) at least one organic solvent different from the aforementioned amine compound and has a pH-value (20° C.) in the range from pH 3.0 to pH 8.5, and;
d) Dissolution of the extracted nucleic acid from the washed separated constituents from step c) by use of a dissolving buffer and collection of the dissolved nucleic acids in a separate receptacle.

The process in this invention is a simple "Bind-Wash-Elute" process. In the context of a "Bind-Wash-Elute" process, the process described in this invention separates nucleic acids by separating nucleic acids together with endotoxins in a fluid sample using established techniques and then removing the majority of the contaminating endotoxin by means of a specially designed washing solution. With this method, it is possible to markedly reduce the endotoxin rapidly and economically, and the eluted nucleic acid, particularly the eluted DNA, can be used directly in subsequent applications depending upon the method used for nucleic acid separation.

A substance is "fluid" if it is present as a liquid under the conditions required for the process described in this invention, in particular at 20° C. and 1013 mbar.

The use of the indefinite article (a, an) or the definite article (the) is—if not otherwise stated in the individual case—not to be taken to limit quantities in the context of the present report. What is meant—if not otherwise stated in the individual case—is a number of at least one (i.e. one or more).

Nucleic acids include RNA and DNA of various chain lengths, especially with more than fifteen nucleotides, such as, for example, single- and double-stranded bacterial, viral, human, animal or plant RNA or DNA, particularly genomic DNA, mitochondrial DNA, plasmids, mRNA, tRNA, rRNA, miRNA and other short RNA-species, in particular with a chain length of 15 to 25 nucleotides. In this invention, "nucleic acid" should be understood to refer particularly to deoxyribonucleic acid (DNA), especially plasmid DNA.

A chemical compound is considered to be "organic" if it contains at least one carbon atom and a hydrogen atom bound covalently to it.

DETAILED DESCRIPTION OF THE INVENTION

The invention further relates to a process for purification of nucleic acids, particularly of plasmid DNA, from a nucleic acid-containing, biologic sample, containing the following steps:
a) Preparation of a fluid sample containing nucleic acid and endotoxin each in dissolved form;
b) Precipitation of at least the nucleic acid and endotoxin from the fluid sample;
c) Washing of the precipitated constituents of the fluid sample from step b) in order to at least partially remove the endotoxin with at least one washing solution which contains
   (i) at least one amine compound with at least two carbon atoms and with a molar mass of 500 g/mol and;
   (ii) at least one organic solvent different from the aforementioned amine compound and has a pH-value (20° C.) in the range from pH 3.0 to pH 8.5 and;
d) Dissolution of the leftover nucleic acid from the washed, separated constituents from step c) by means of a dissolving buffer and collection of the dissolved nucleic acids in a separate receptacle, with the process being characterized by the washing solution of step c), which contains the organic amine compound in a concentration of 200 mmol/L to 1,000 mmol/L.

In the context of this invention, an at least partial removal is present if, in each case with respect to the total endotoxin content of the liquid sample, there has been removal of at least 50% by weight of the endotoxin, especially favored by removal of at least 60% by weight and particularly favored by removal of at least 70% by weight of the endotoxin.

A biologic sample is used to make the fluid nucleic acid- and endotoxin-containing sample. Any biologic material, which contains both nucleic acids and endotoxin is suitable, including bacterial cultures, animal or human tissues, tissue components, bodily fluids such as saliva, sputum, cerebrospinal fluid, whole blood, serum or plasma. Bacteria, yeasts and other fungi or viruses are also considered to be "test material", as are PCR-amplification reactions which contain primer and DNA fragments, or cell culture remnants. Test material can also include samples of environmental material or food samples. Artificial sample material, e.g. with synthetically or in-vitro generated nucleic acids, also falls into the area of applicability of the present invention.

To prepare a fluid sample containing nucleic acids and endotoxin each in dissolved form according to step a) of the process described in this invention, the biologic sample may first be opened, i.e. lysed, in order to release the nucleic acids and endotoxin from the material. The opening may take the form of mechanical, chemical and/or enzymatic disruption. The opening of the biologic sample is often supported by using suitable buffer chemistry containing, for example, detergents. Suitable lysis conditions are known to the expert.

In step b) of the process described in the present invention, the nucleic acids together with endotoxin are precipitated from the liquid sample using any process the expert is familiar with.

The process described in this invention is therefore not restricted to a particular precipitation technique. The state of the art contains various processes which can be used and are known to the expert. These include, for example, the use of chaotropic salts, the use of anti-chaotropic salts, precipitations (e.g. precipitation with polyethylene glycol or lower alcohols), filtration, the use of hydrophobic interactions to bind nucleic acids to a carrier material and other processes.

A preferred form of precipitation is characterized by the fact that in that in step b) at least nucleic acids and endotoxin are precipitated onto the surface of a solid carrier material by binding, in particular by adsorption or precipitation. It is again particularly favored if the sample in step b) is precipitated onto the carrier material by mixing with a binding buffer.

The binding buffer preferentially contains at least a chaotropic salt and/or at least one monoalcohol with up to 16 carbon atoms.

According to current theory, chaotropic salts destroy the ordered water structure around compounds dissolved in water. Chaotropic salts are thus defined in that they denature proteins, increase the solubility of unipolar substances in water and destroy hydrophobic interactions. It is known that nucleic acid in the presence of chaotropic salts binds reversibly to carrier materials, especially silicates and other inorganic carrier materials. The chaotropic salts disrupt the hydrate shell of the nucleic acid and generate a hydrophobic microenvironment. Under these conditions both nucleic acid and endotoxin bind to the solid carrier material, while proteins and other contaminants do not bind and are washed out. The strength of the chaotropic nature of the salt is described in the so-called Hofmeister series.

The binding buffer contains chaotropic salt preferably in a concentration of 1 to 6 mol/L.

In the context of the present invention, sodium perchlorate, sodium iodide, guanidinium isothiocyanate, guanidinium hydrochloride, potassium thiocyanate, guanidinium nitrate, guanidinium carbonate, urea or also combinations of these are preferentially used as chaotropic salts.

It is particularly preferred in this invention if the binding buffer contains at least one chaotropic salt or at least one monoalcohol with up to 16 carbon atoms or an organic polymer.

The precipitation of nucleic acid and endotoxin from the sample can, as stated previously, be undertaken by accretion of the aforementioned biomolecules onto a solid carrier material. The solid carrier material is preferably chosen from mineral carrier materials, in particular quartz fibers, silica, glass, aluminum oxide, zeolite, titanium dioxide, zirconium dioxide or combinations of these. These carriers may be present in particulate form, above all as magnetic or magnetizable particles, particularly magnet beads. Further, the solid carrier material may be applied in the form of fibers, sponges, foams and in particular in the form of chips or membranes. In the preferred method, the solid carrier material is arranged as a chromatographic column. Here, the solid carrier material can take the form of a packed column and/or a membrane, especially using the above named mineral carrier materials.

The precipitation of nucleic acid and endotoxin onto the solid carrier material can be brought about by bringing the sample into contact with the solid carrier material. If magnetic or magnetizable particles, particularly magnet beads, are used as the carrier material, these can also be added directly to the sample. Along with addition of the particles, the binding conditions can be further improved by the addition of a binding buffer (vide supra) to the sample and/or the separation of the bound particles can be facilitated by centrifugation, filtration, vacuum filtration or magnetic separation.

If mineral carrier materials such as silica are used as the solid carrier material, it is preferable to first mix binding buffer (vide supra) into the sample in order to improve the binding conditions.

Under the invention, it is particularly preferable for the precipitation step b) of the process described in this invention to use a solid carrier material containing silica in combination with a binding buffer (in particular the binding buffers identified as the preferred ones (vide supra), and most preferably a binding buffer containing at least one chaotropic salt or its preferred embodiments (vide supra)).

Purification processes with the sequence of binding of the product, one or more wash steps and finally the elution of the cleaned product are called "Bind-wash-elute" processes.

Usually, centrifuge columns are used in "Bind-wash-elute" processes using silica or alternative mineral carrier materials as the solid carrier material. Since the individual processing steps such as binding of nucleic acid, are generally performed in small laboratory centrifuges, the corresponding columns are known as "Minispin" columns. These columns are well known in the industry and include small columns which, for example, fit into a 1.5 ml Eppendorf tube and can be processed in this using a microcentrifuge.

Under the invention, it is especially preferred if in step b) of the process described in the invention the solid carrier material is arranged in the form of a "Minispin" column for use in a laboratory centrifuge.

It is preferred that the mixture of nucleic acid and endotoxin which precipitated onto the carrier material is passed in bound form into step c) of the process described in this invention.

As another favored possibility for precipitation in step b), at least the nucleic acid and endotoxin can be precipitated from the fluid sample as solids by direct precipitation. This can be achieved by adding a precipitant to the fluid sample which causes nucleic acid and endotoxin to precipitate as solids out of the solution. The precipitant preferably contains at least one compound selected from tripropylene glycol (preferably in combination with a $(C_1-C_4)$-alcohol (especially preferred are methanol, ethanol, n-propanol or isopropanol, most favored is ethanol)), polyethylene glycols with a molecular weight between 300 and 10,000 g/mol, polypropylene glycols with a molecular weight between 300 and 10,000 g/mol, cationic detergents (such as hexadecyltrimethylammoniumbromide (CTAB), pyridinium salts orquaternary ammonium compounds with a long, chain-like hydrocarbon residue $(C_6-C_{18})$ and three residues, chosen from short hydrocarbon residues $(C_1-C_3)$ orhydrogen), ethanol, n-propanol, isopropanol or combinations of these.

If (where appropriate by the addition of the precipitant) nucleic acid and endotoxin have precipitated as solids from the fluid sample, it is again preferred that the precipitated nucleic acid and endotoxin as solids i) are collected by filtration on the surface of a solid carrier material, or ii) are compacted by centrifugation, in either case to separate them from the parent solution.

The carrier material for collection of the precipitated solid should, in accordance with particularly favored embodiments, i) again preferably be selected from mineral carrier materials, in particular quartz fibers, silica gel, glass, aluminum oxide, zeolite, titanium dioxide, zirconium dioxide or combinations of these.

Under this invention it is preferred that for filtration, the solid carrier material be selected from mineral carrier materials, in particular quartz fibers, silica gel, glass, aluminum oxide, zeolite, titanium dioxide, zirconium dioxide or combinations of these, and that for precipitation of nucleic acid and endotoxin at least one precipitant be used, in particular at least one of the favored precipitants (vide supra), most especially tripropylene glycol (preferably in combination with a $(C_1-C_4)$-alcohol (preferably methanol, ethanol, n-propanol or isopropanol)). An especially favored precipitant contains tripropylene glycol and ethanol.

If the aforementioned solid has been compacted in a vessel by centrifugation as in alternative ii), then it will be located on the walls of the vessel. The residual parent solution can then be removed for example by means of a pipette.

What is left under alternative i) and alternative ii) is the aforementioned precipitated solid, which is preferably either in the form of a filter cake on the carrier material or as a compacted precipitate on the vessel wall, and in either case it can be passed in this form directly into step c).

In step c) of the process described in this invention, the precipitated mixture of at least nucleic acid and endotoxin is washed with a special washing solution. This washes out the majority of the endotoxin in the precipitated mixture, whilst nucleic acid is predominantly left behind.

The washing solution used in step c) contains an obligatory special organic amine compound (vide supra). This special organic amine compound is chosen, for example, whilst complying with the aforementioned obligatory characteristics, from at least one compound of the group consisting of compounds containing one amino group, compounds with at least two amino groups, compounds with at least one amino group and at least one hydroxyl group, compounds with at least two amino groups and at least one hydroxyl group (especially favorably with at least one compound from the group consisting of compounds with an amino group, compounds with at least one amino group and at least one hydroxyl group).

Under the invention, it is preferred if the aforementioned amine compound has a molar mass of 80 to 500 g/mol.

To improve its solubility in water, it is preferable if the amine compound possesses at least two hydroxyl groups.

Especially suitable organic amine compounds have substituted hydrocarbon residues with 1 to 6 carbon atoms. Suitable substituents include particularly hydroxy or alkoxy groups.

The organic amine compound in the washing solution is selected for example from triethylamine, triethanolamine, 2-amino-2-(hydroxymethyl)-propane-1,3-diol (TRIS), 2,2-bis(hydroxymethyl)-2,2',2"-nitrilotriethanol (BIS-TRIS), 1,3-bis[tris(hydroxymethyl)methyl-amino]propane (BIS-TRIS propane), diisopropylamine, triisopropylamine, or combinations of these.

Under this invention, it is particularly preferred that the organic amine compound in the washing solution in step c) be chosen from at least one compound with the general formula (I), (I)

wherein $R^1$, $R^2$ and $R^3$ independently of each other stand for a hydrogen atom, a ($C_1$ to $C_6$)-alkyl group, a ($C_1$ to $C_6$)-monohydroxyalkyl group, a ($C_2$ to $C_6$)-dihydroxyalkyl group, a ($C_3$ to $C_6$)-trihydroxyalkyl group,
  with the provision that the organic amine compound of formula (I) have a molar mass of 500 g/mol, and at least one of the residues $R^1$, $R^2$ and $R^3$ differs from a hydrogen atom.

It is particularly preferable when $R^1$, $R^2$ and $R^3$ independently to formula (I) represent independently of each other a hydrogen atom, a ($C_1$ to $C_6$)-alkyl group, a ($C_2$ to $C_6$)-monohydroxyalkyl group, a ($C_3$ to $C_6$)-dihydroxyalkyl group, a ($C_4$ to $C_6$)-trihydroxyalkyl group, Especially suitable amine compounds according to formula (I) have a molar mass of 80 to 500 g/mol.

It is especially favorable to select the organic amine compound for the washing solution from triethylamine, triethanolamine, 2-amino-2-(hydroxymethyl)-propane-1,3-diol (TRIS), 2,2-bis(hydroxymethyl)-2,2',2"-nitrilotriethanol (BIS-TRIS), 1,3-bis[tris(hydroxymethyl)methyl-amino] propane (BIS-TRIS propane) or combinations of these.

Particularly good results are seen when the washing solution in step c) contains the aforementioned amine compound, especially the preferred types, in a concentration of 5 mmol/L to 1,000 mmol/L, preferably from 200 mmol/L to 800 mmol/L, more preferably from 200 mmol/L to 700 mmol/L, even more preferably 250 mmol/L to 650 mmol/L. The preferred concentrations referred to above and in the following are determined relative to the quantity of the amine compound used in making the washing solution.

If the washing solution used in this invention contains the aforementioned organic amine compounds in small quantities, i.e. less than 100 mmol/L, then the removal of endotoxin which is the goal of this invention can be improved by the addition of a chaotropic salt (for preferred types vide supra). Here it is again preferable that the total quantity of chaotropic salt added is between 1 mol/L and 6 mol/L, especially favorable being 1 mol/L to 4 mol/L. Once again, it is preferable if the washing solution specified in this invention which contains at least 100 mmol/L of the aforementioned organic amine compound, additionally contains chaotropic salt preferably at a concentration of 0 to 1 mol/L, more preferably 0 to 0.5 mol/L, most preferably 0 to 0.1 mol/L.

The washing solution of step c) must contain one organic solvent different from the aforementioned amine compound. The organic solvent should preferably make up 20 to 80% by weight of the washing solution relative to the total weight of the washing solution.

It has proven to be beneficial if the washing solution's organic solvent contains at least one monoalcohol. It is particularly favorable if the washing solution contains as its organic solvent at least one $C_1$-$C_6$-monoalcohol, particularly ethanol, isopropanol or combinations of these. It is again particularly preferable if the washing solution contains the $C_1$-$C_6$-monoalcohol in a total amount of 20 to 80% by weight relative to the total weight of the washing solution, preferably 30 to 80% by weight, more preferably 35 to 80% by weight, most preferably 38 to 80% by weight.

In one preferred embodiment, the $C_1$-$C_6$-monoalcohol is isopropanol and the washing solution contains this in a total quantity of 35 to 80% by weight relative to the total weight of the washing solution.

In an alternative preferred embodiment, the $C_1$-$C_6$-monoalcohol is ethanol and the washing solution contains this in a total quantity of 65 to 80% by weight relative to the total weight of the washing solution.

These alcohol concentrations are preferred since the nucleic acids thereby precipitated remain in precipitated form and so when washed with the washing solution they are not inadvertently removed in solution. In this way, the eventual nucleic acid yield is increased.

The washing solution used for step c) must have a pH-value (20° C.) in the range from pH 3.0 to 8.5, preferably from pH 4.0 to pH 8.5. For optimal purification results and an improved nucleic acid yield, the aforementioned washing solution should have a pH-value (20° C.) in the range from pH 3.0 to 7.5, from pH 3.0 to 7.0, from pH 4.0 to 7.5, from pH 4.0 to 7.0, from pH 5.0 to 7.5 or especially favorably from pH 5.0 to pH 7.0.

In a preferred embodiment of the washing solution used in this invention, the nitrogen atom in the amino group(s) of the aforementioned amine compound is at least 50% protonated, especially favorably at least 60% and most favorably at least 70% protonated. For these purposes, the pH-value of the washing solution is preferably is chosen within the range of the preset pH value in such a way that the aforementioned nitrogen atom of the amino group(s) has a degree of protonation of at least 50%, preferably at least 60% and particularly favorably at least 70%. As a model system for preparing such a preferred washing solution, an aqueous solution of the appropriate quantity of the amine compound to be made is taken as the initial concentration and the calculated pH-value (20° C.) is set for the required degree of protonation using the Henderson-Hasselbalch equation:

$$pH=pKs+\log_{10}((1-a)/a)$$

with $a$=[degree of protonation of the amine compound in %]/100

The organic amine compounds, with the aforementioned degree of protonation, are again particularly favorably contained in the washing solution in concentrations previously defined as preferred, namely 5 mmol/L to 1,000 mmol/L, especially 200 mmol/L to 800 mmol/L, more favorably 200 mmol/L to 700 mmol/L, especially favorably 250 mmol/L to 650 mmol/L.

When using at least TRIS as the organic amine compound, it has proved to be optimal if the washing solution has a pH-value (20° C.) in the range from pH 6.0 to pH 8.5, more especially from pH 6.0 to 7.0. Once again it is preferable to set the concentration of TRIS in the washing solution to be at least 80 mmol/L, most preferably at least 100 mmol/L, further preferably at least 200 mmol/L, especially preferably at least 250 mmol/L. The upper limit of the total concentration of the aforementioned organic amine compound can be advantageously set at 1,000 mmol/L, especially 800 mmol/L, more preferably 700 mmol/L, especially favorably 650 mmol/L.

When using BIS-TRIS as the organic amine compound it has proved to be optimal if the washing solution has a pH-value (20° C.) in the range from pH 5.0 to pH 8.0, especially from pH 5.5 to pH 7.5, particularly favorably from pH 5.0 to pH 7.0. Once again, it is particularly favored if the BIS-TRIS has a concentration in the washing solution of at least 80 mmol/L, very favorably of at least 100 mmol/L, also favorably of at least 200 mmol/L, especially favorably of at least 250 mmol/L. The upper limit of the total concentration of the aforementioned organic amine compound in this embodiment can be advantageously set at 1,000 mmol/L, especially 800 mmol/L, more preferably 700 mmol/L, especially favorably 650 mmol/L.

On occasion, additional washing steps of the precipitated constituents from step b) may precede or follow the washing step c) described in this invention. These additional washing steps of the precipitated nucleic acid serve to preferentially remove contaminants other than endotoxin.

In step d) of the process described in this invention, a dissolving buffer is used to dissolve the remaining nucleic acid from the washed, precipitated constituents from step c) and to collect the dissolved amino acids in a separate receptacle.

In the dissolving step, the remaining precipitated nucleic acid is dissolved in the dissolving buffer and removed from the solid carrier material. Preferred dissolving buffers which are particularly suited to the dissolution of the remaining precipitated nucleic acid, have a low ionic strength. As an example, a suitable dissolving buffer contains 5 to 10 mM TRIS (on occasion in combination with up to 1 mM ethylenediaminetetraacetic acid (EDTA)).

Dissolution according to step d) of the process described in this invention is preferably achieved by means of rinsing of the solid carrier material with the dissolving buffer followed by collection of the dissolving buffer in a separate receptacle. The rinsing is preferably achieved by a flow of the dissolving buffer through the solid carrier material. The direction of flow is determined by the application of a vacuum or by centrifugation.

The present invention further relates to the use of a washing solution which contains
(i) at least one amine compound with at least two carbon atoms and with a molar mass of 500 g/mol and
(ii) at least one organic solvent different from the aforementioned amine compound and
has a pH-value (20° C.) in the range from pH 3.0 to pH 8.5, in order to at least partially remove endotoxin from a nucleic acid-containing sample.

In such cases, those embodiments of the washing solution, which were described in the methodology of the original subject matter of the discovery are especially preferred for use (vide supra).

The present invention further relates to the use of a washing solution which contains
(i) at least one amine compound with at least two carbon atoms and with a molar mass of 500 g/mol and
(ii) at least one organic solvent different from the aforementioned amine compound and
has a pH-value (20° C.) in the range from pH 3.0 to pH 8.5
in order to at least partially remove endotoxins from a nucleic acid-containing sample, wherein the washing solution is characterized by its content of the aforementioned organic amine compound in a concentration of 200 mmol/L to 1,000 mmol/L.

The nucleic acids contained in the sample can be those nucleic acids (particularly plasmid DNA) described in the original subject matter of the discovery.

The washing solution is particularly suited to the use described in this invention if the nucleic acid and the endotoxin are present bound to the surface of a solid carrier material, particularly if adsorbed.

The invention relates to a kit used for purifying nucleic acids, particularly plasmid DNA, comprising a washing solution which contains
(i) at least one amine compound with at least two carbon atoms and with a molar mass of 500 g/mol and
(ii) at least one organic solvent different from the aforementioned amine compound and
has a pH-value (20° C.) in the range from pH 3.0 to pH 8.5
as well as at least one additional component selected from an instruction manual in order to perform one of the processes described in the original subject matter of the discovery, binding buffer and dissolving buffer in order to dissolve the nucleic acids which have been at least partially cleansed of endotoxins.

All preferred embodiments of the process described in the original subject matter of the discovery apply equally to the process described in the instruction manual of the kits.

The invention also relates to a kit for purifying nucleic acids, particularly plasmid DNA, comprising a washing solution, which contains
(i) at least one amine compound with at least two carbon atoms and with a molar mass of 500 g/mol and (ii) at least one organic solvent different from the aforementioned amine compound and
has a pH-value (20° C.) in the range from pH 3.0 to pH 8.5 as well as at least one additional component chosen from an instruction manual in order to perform one of the processes described in the original subject matter of the discovery, binding buffer and dissolving buffer to dissolve the nucleic acids which have been at least partially cleansed of endotoxins, where the washing solution is characterized by its content of the aforementioned amine compound in a concentration of from 200 mmol/L to 1000 mmol/L.

All preferred embodiments of the binding buffer in the original subject matter of the discovery apply equally to the kits of the third subject matter of the discovery.

All preferred embodiments of the dissolving buffer in the original subject matter of the discovery apply equally to the kits of the third subject matter of the discovery.

The invention relates, in particular, to the following embodiments:

In a first embodiment, the invention relates to a process for the purification of nucleic acids, particularly of plasmid DNA, from a biologic sample containing nucleic acid comprising the following steps:
  a) Preparation of a fluid sample containing nucleic acid and endotoxin each in dissolved form;
  b) Precipitation of at least nucleic acid and endotoxin from the fluid sample;
  c) Washing of the precipitated constituents of the fluid sample from step b) in order to at least partially remove the endotoxin with at least one washing solution which contains
    (i) at least one amine compound with at least two carbon atoms and with a molar mass of 500 g/mol and;
    (ii) at least one organic solvent different from the aforementioned amine compound and has a pH-value (20° C.) in the range from pH 3.0 to pH 8.5 and;
  d) Dissolution of the leftover amino acid in the washed, precipitated constituents from step c) using a dissolving buffer and collection of the dissolved nucleic acids in a separate receptacle.

In a second embodiment, the invention relates to a process according to embodiment 1 characterized by the fact that in step b) nucleic acid and endotoxin are precipitated by binding onto the surface of a solid carrier material, particularly by adsorption or precipitation.

In a third embodiment, the invention relates to processes according to embodiment 2 characterized by the fact that in step b) the sample is mixed with a binding buffer in order to cause it to precipitate onto the carrier material.

In a fourth embodiment, the invention relates to processes according to embodiment 1 characterized by the fact that in step b) at least nucleic acid and endotoxin are deposited as solids by precipitation.

In a fifth embodiment, the invention relates to processes according to embodiment 4 characterized by the fact that the nucleic acid and endotoxin precipitated as solids are
  i) collected on the surface of a solid carrier material, or
  ii) compacted by centrifugation,
and each removed from the parent solution.

In a sixth embodiment, the invention relates to a process according to embodiments 2, 3 or 5 characterized by the fact that the carrier material is chosen from mineral carrier materials, particularly quartz fibers, silica, glass, aluminum oxide, zeolite, titanium dioxide, zirconium dioxide or combinations of these.

In a seventh embodiment, the invention relates to a process according to one of the previous embodiments characterized by the fact that the organic amine compound of the washing solution in step c) is chosen with at least one compound of general formula (I), wherein $R^1$, $R^2$ and $R^3$ independently of each other stand for a hydrogen atom, a ($C_1$ to $C_6$)-alkyl group, a ($C_1$ to $C_6$)-monohydroxyalkyl group, a ($C_2$ to $C_6$)-dihydroxyalkyl group, a ($C_3$ to $C_6$)-trihydroxyalkyl group,
with the provision that the organic amine of formula (I) have a molar mass of 500 g/mol, and at least one of the residues $R^1$, $R^2$ and $R^3$ differs from a hydrogen atom.

In an eighth embodiment, the invention relates to a process according to one of the previous embodiments characterized by the fact that the organic amine compound used in the wash solution is selected from triethylamine, triethanolamine, 2-amino-2-(hydroxymethyl)-propane-1,3-diol (TRIS), 2,2-bis(hydroxy-methyl)-2,2',2"-nitrilotriethanol (BIS-TRIS), 1,3-bis[tris(hydroxymethyl)methylamino]propane (BIS-TRIS propane) or combinations of these.

In a ninth embodiment, the invention relates to a process according to one of the previous embodiments characterized by the fact that the washing solution used in step c) contains the aforementioned amine compound in a concentration of from 5 mmol/L to 1,000 mmol/L, particularly from 200 mmol/L to 800 mmol/L.

In a tenth embodiment, the invention relates to a process according to one of the previous embodiments characterized by the fact that the nitrogen atom of the amino group(s) in the aforementioned amine compound is(are) at least 50% protonated, preferably at least 60% protonated, especially preferably at least 70% protonated.

In an eleventh embodiment, the invention relates to a process according to one of the previous embodiments characterized by the fact that the washing solution used in step c) contains at least one $C_1$-$C_6$-monoalcohol, particularly ethanol, isopropanol or combinations of these, as the solvent.

In a twelfth embodiment, the invention relates to a process according to embodiment 11 characterized by the fact that the washing solution contains the $C_1$-$C_6$-monoalcohol in a total amount of 20 to 80% by weight relative to the total weight of the washing solution.

In a thirteenth embodiment, the invention relates to a process according to one of the previous embodiments characterized by the fact that the washing solution used in step c) has a pH-value (20° C.) in the range from pH 5.0 to pH 7.0.

In a fourteenth embodiment, the invention relates to a process according to one of the previous embodiments characterized by the fact that, in the setting of an at least partial removal, as a proportion of the total amount of endotoxin in the fluid sample at least 50% by weight, preferably at least 60% by weight, especially preferably at least 70% by weight of the endotoxin is removed.

In a fifteenth embodiment, the invention relates to the use of a washing solution, which contains
(i) at least one amine compound with at least two carbon atoms and with a molar mass of 500 g/mol and
(ii) at least one organic solvent different from the aforementioned amine compound and
has a pH-value (20° C.) in the range from pH 3.0 to pH 8.5
in order to at least partially remove endotoxins from a sample containing nucleic acid.

In a sixteenth embodiment, the invention relates to a use according to embodiment 15 characterized by the fact that the nucleic acid and the endotoxin are present bound to the surface of a solid carrier material, in particular adsorbed to it.

In a seventeenth embodiment, the invention relates to a kit for purifying nucleic acids, particularly plasmid DNA, comprising a washing solution, which contains
(i) at least one amine compound with at least two carbon atoms and with a molar mass of ≤500 g/mol and
(ii) at least one organic solvent different from the aforementioned amine compound and
has a pH-value (20° C.) in the range from pH 3.0 to pH 8.5
as well as at least one additional component chosen from an instruction manual in order to perform a process according to one of the embodiments 1 to 14, a binding buffer and a dissolving buffer in order to dissolve nucleic acids which have been at least partially cleansed of endotoxins.

EXAMPLES

Example 1

An overnight culture of E. coli DH5α™, transformed with the plasmid pcDNA™3.1(+) was prepared in an ampicillin-containing nutrient medium. Varying 1 ml, 2 ml and 3 ml aliquots of the culture were centrifuged at 10,000×g for 5 min and the supernatant was discarded. The pellets were resuspended in a resuspension buffer containing EDTA, Tris and RNase A, lysed with a lysis buffer containing NaOH and SDS and neutralized with a neutralization buffer containing potassium acetate. The lysates were cleared by centrifugation at 10,000×g for 10 min and the clear supernatant was mixed with a guanidinium hydrochloride solution. The mixture was filled onto spin columns containing silica layers and flushed through the silica carrier material by centrifugation at 10,000×g for 1 min into a receptacle. Following this, each pelleted bacterial culture volume was filled onto spin columns with a washing solution with the following variations:
no washing solution
30% isopropanol, 7 mM TRIS, 4.55 M guanidinium hydrochloride, pH 7.5
50% isopropanol, 200 mM BIS-TRIS, pH 5.5
The columns were centrifuged at 10,000×g for 1 min, with the washing solution being flushed through the silica carrier material into a receptacle. This process was repeated once. Thereafter a washing step was performed using a known washing solution containing 80% ethanol. Again, in order to flush through the silica carrier material, it was centrifuged at 10,000×g for 1 min. To dry them the columns were centrifuged empty at 10,000×g for 1 min. The DNA was eluted after addition of 100 µl dissolving buffer (water with 5 mM Tris-Cl, pH 8.5) again by centrifugation at 10,000×g for 1 min. The yield was measured with a photometer by measuring extinction at 260 nm, and the endotoxin content measured using the pyrochrome LAL-Test (Cape Cod).

The following table shows the measured results:

| Washing solution | µg DNA/ eluate | relative yield/% | EU/ µg | Endo- toxin- removal/% |
|---|---|---|---|---|
| 1 ml bacterial culture | | | | |
| no special wash step | 12.9 | 100% | 125 | 0 |
| 30% isopropanol, 7 mM TRIS, 4.55M Guanidinium hydrochloride, pH 7.5 | 13.5 | 105% | 15 | 88 |
| 50% isopropanol + 200 mM BIS-TRIS, pH 5.5 | 12.1 | 94% | 14 | 89 |
| 2 ml bacterial culture | | | | |
| without a special wash step | 16.9 | 100% | 632 | 0 |
| 30% isopropanol, 7 mM TRIS, 4.55M Guanidinium hydrochloride, pH 7.5 | 15.4 | 91% | 102 | 84 |
| 50% isopropanol + 200 mM BIS-TRIS, pH 5.5 | 15.0 | 89% | 14 | 98 |
| 3 ml bacterial culture | | | | |
| without a special wash step | 18.8 | 100% | 914 | 0 |
| 30% isopropanol, 7 mM TRIS, 4.55M Guanidinium hydrochloride, pH 7.5 | 17.1 | 91% | 128 | 86 |
| 50% isopropanol + 200 mM BIS-TRIS, pH 5.5 | 16.7 | 89% | 12 | 99 |

Even the presence of small quantities of TRIS was sufficient to markedly reduce the endotoxin concentration of the eluate. No significant effect on the DNA yield was seen.

Example 2

An overnight culture of E. coli DH5α™, transformed with the plasmid pc DNA™3.1(+) was prepared in an ampicillin-containing nutrient medium. 25 ml aliquots of the culture were centrifuged at 4,500×g for 10 min, and the supernatant was discarded. The pellets were resuspended in a resuspension buffer containing EDTA, Tris and RNase A, lysed with a lysis buffer containing NaOH and SDS and neutralized with a neutralization buffer containing potassium acetate. The lysates were cleared by centrifugation over a filter column containing polyethylene chips and silica at 3,000×g for 2 min and the clear effluent was mixed with a precipitation solution containing 85% tripropylene glycol and 2.5% ethanol. The mixture was filled onto columns containing silica layers and pulled through the silica carrier material into a receptacle by the application of a negative pressure of −0.3 bar. Following this, it was washed with washing solutions containing 200 mM or 400 mM TRIS or BIS-TRIS at pH 7 or pH 8 for TRIS and pH 5.5 or pH 6.5 for BIS-TRIS, as well as a control with no washing step, and washed with 50% isopropanol with no further additives and then rinsed with a known washing solution containing 80% ethanol. Again, a negative pressure of −0.3 bar was used to wash through the silica. To dry them, the columns were centrifuged empty at 10,000×g for 1 min. The DNA was eluted after addition of 200 µl dissolving buffer (water with 5 mM Tris-Cl, pH 8.5) again by centrifugation at 10,000×g for 1 min. The yield was measured with a photometer by measuring extinction at 260 nm, and the endotoxin content measured using the pyrochrome LAL-Test (Cape Cod).

The following table shows the measured results:

| Washing solution | μg DNA/ eluate | EU/μg | Endotoxin removal % |
|---|---|---|---|
| TRIS pH 7.0 | | | |
| 200 mM | 79 | 25 | 80 |
| 400 mM | 73 | 13 | 89 |
| TRIS pH 8.0 | | | |
| 200 mM | 73 | 18 | 86 |
| 400 mM | 78 | 17 | 86 |
| BIS-TRIS pH 5.5 | | | |
| 200 mM | 73 | 12 | 90 |
| 400 mM | 74 | 18 | 85 |
| BIS-TRIS pH 6.5 | | | |
| 200 mM | 70 | 5 | 96 |
| 400 mM | 66 | 6 | 94 |
| without wash step | 89 | 123 | 0 |
| 50% Isopropanol | 13 | | |

The washing solution not prescribed in this invention consisting of a solution of 50% isopropanol was not on its own able to hold the DNA on the column.

Example 3

An overnight culture of *E. coli* DH5α™, transformed with the plasmid pc DNA™3.1(+) was prepared in an ampicillin-containing culture medium. 50 ml aliquots of the culture were centrifuged at 4,500×g for 10 min, and the supernatant was discarded. The pellets were resuspended in a resuspension buffer containing EDTA, Tris and RNase A, lysed with a lysis buffer containing NaOH and SDS and neutralized with a neutralization buffer containing potassium acetate. The lysate was cleared by centrifugation over a filter column containing polyethylene chips and silica at 3,000×g for 2 min and the cleared effluent was mixed with a precipitation solution containing 85% tripropyleneglycol and 2.5% ethanol. The mixture was filled onto columns containing silica sheets and drawn into a receptacle by applying a negative pressure of −0.3 bar. Following this, washing solutions of the following constitution were filled onto the columns and drawn through the silica into a receptacle by applying a suction pressure of −0.3 bar:
  no washing step
  50% isopropanol+200 mM BIS-TRIS, pH 6.0 (as in this invention)
  50% isopropanol+100 mM NaCl
  50% isopropanol+500 mM NaCl
  50% isopropanol+1 M NaCl
  50% isopropanol+1 M guanidine HCl
  50% isopropanol+2 M guanidine HCl
  50% isopropanol+3 M guanidine HCl
  50% isopropanol+100 mM sodium acetate, pH 5.0
  50% isopropanol+250 mM sodium acetate, pH 5.0
  50% isopropanol+500 mM sodium acetate, pH 5.0

Finally, the columns were rinsed with a known washing solution containing 80% ethanol. Again, a suction pressure of −0.3 bar was used to wash through the silica carrier material. For drying, the columns were centrifuged empty at 10,000×g for 1 min. The DNA was eluted by the addition of 200 μl precipitation buffer (water with 5 mM Tris-Cl, pH 8.5), again whilst centrifuging at 10,000×g for 1 min. The yield was determined with a photometer by measuring the extinction at 260 nm, the endotoxin content by measurement using the pyrochrome LAL-Test (Cape Cod).

The following measurements were obtained:

| Washing solution | μg DNA/ eluate | relative yield/% | EU/μg | endotoxin-removal/% |
|---|---|---|---|---|
| No wash step | 635 | 100% | 473 | 0 |
| 50% isopropanol + 200 mM BIS-TRIS, pH 6.0 | 597 | 94% | 34 | 93 |
| 50% isopropanol + 100 mM sodium chloride | 625 | 98% | 448 | 5 |
| 50% isopropanol + 500 mM sodium chloride | 603 | 95% | 511 | 0 |
| 50% isopropanol + 1000 Mm sodium chloride | 617 | 97% | 305 | 36 |
| 50% isopropanol + 1M guanidine HCl | 617 | 97% | 317 | 33 |
| 50% isopropanol + 2M guanidine HCl | 612 | 96% | 464 | 2 |
| 50% isopropanol + 3M guanidine HCl | 586 | 92% | 154 | 67 |
| 50% isopropanol + 100 mM sodium acetate, pH 5.0 | 641 | 101% | 369 | 22 |
| 50% isopropanol + 250 mM sodium acetate, pH 5.0 | 644 | 101% | 388 | 18 |
| 50% isopropanol + 500 mM sodium acetate, pH 5.0 | 606 | 95% | 275 | 42 |

It can be clearly seen that in all cases the salt concentration was sufficient to keep the DNA on the column during the washing step. A significant removal of endotoxin was neither achieved by salt nor by isopropanol alone, nor by means of a pH-related effect. Acetate can also only incompletely separate the endotoxin.

Comparative Tests Against WO 2005/111059 A2

The following comparative tests show a comparison of the invention to the state of the art in the form of WO 2005/111059 A2. Initially two washing solutions were made as per WO 2005/111059 A2:

Washing Solution 1:

| 100 mM Tris | 1.211 g/100 mL |
|---|---|
| 4.5M guanidine hydrochloride | 43.0 g/100 mL |
| Dissolve in H₂O | |
| Adjustment to pH 6.9 with acetic acid | |
| 25% isopropanol | 25 mL/100 mL |
| to 100 mL with H₂O | |

Washing Solution 2:

| 10 mM Tris | 0.121 g/100 mL |
|---|---|
| 10 mM NaCl | 0.058 g/100 mL |
| Dissolve in H₂O | |
| Adjustment to pH 8.0 with HCl | |
| 80% ethanol | 80 mL/100 mL |
| to 100 mL with H₂O | |

For the following tests, the following chemicals were also used:
  Resuspension buffer: 50 mM Tris-Cl, 10 mM EDTA, pH 8.0, 400 μg/mL RNase A
  Lysis buffer: 1% SDS, 200 mM NaOH
  Neutralization buffer: 2.8 M potassium acetate, pH 5.1
  Binding buffer: 8 M guanidine hydrochloride
  Precipitation solution: 85% tripropyleneglycol, 2.5% ethanol
  Endotoxin removal buffer: 8% triethanolamine, 50% isopropanol, pH 6.0

Alcoholic wash buffer: 2.5 mM Tris, 20 mM NaCl, 80% ethanol, pH 7.5

Comparative Test 1

300 mL LB-medium and 100 µg/mL Ampicillin were inoculated with *E. coli* Top 10, containing the plasmid pc DNATM3.1 (+) and incubated overnight at 37° C. on a shaker. After 16 hours of incubation an OD600 of 4.6 was measured. The culture was divided into six 50 mL aliquots which were separated by centrifugation at 6,000×g for 5 min into a bacterial pellet and supernatant.

The supernatants were discarded and the bacterial pellets were each taken up into 5 mL of resuspension buffer. Lysis was achieved by the addition of 5 mL lysis buffer to each and incubation at room temperature for 2 minutes. A precipitate was produced by the addition of 5 mL neutralization buffer to each, which was removed by means of centrifugation over a filter column containing PE-filter chips and silica paper at 3,000×g for 2 minutes. The clear supernatants containing the released plasmids were pooled, mixed by vortexing and re-aliquoted into 6×12 mL samples.

3 mL of binding buffer were added to each 12-mL master lysate and mixed by vortexing. The concentration of chaotropic salt at effectively 1.6 M guanidine hydrochloride corresponded to the concentration recommended in D1.

The batches were loaded onto columns filled with three layers of silica paper (diameter of the filter: 7.25 mm) and were to have been drawn through the silica membrane by the application of a vacuum (900 mbar reduction of pressure compared to normal pressure). However, after a few milliliters the columns blocked completely.

Comparative Test 2

300 mL LB-medium plus 100 µg/mL Ampicillin were inoculated with *E. coli* Top 10 containing the plasmid pcDNATM3.1 (+) and incubated on a shaker at 37° C. over night. After 16 hours of incubation an OD600 of 4.6 was measured. The culture was divided into six 50 mL aliquots which were separated into bacterial pellets and supernatant by centrifugation at 6,000×g for 5 min.

The supernatants were discarded and the bacterial pellets were each taken up into 5 mL of resuspension buffer. Lysis was achieved by the addition to each of 5 mL lysis buffer and incubation at room temperature for 2 minutes. A precipitate was produced by the addition to each of 5 mL neutralization buffer, which was removed by means of centrifugation over a filter column containing PE-filter chips and silica paper at 3,000×g for 2 minutes. The clear supernatants containing the released plasmids were pooled, mixed by vortexing and re-aliquoted into 6×12 mL samples. To each 12 ml of master lysate was added 6 mL of precipitation solution and these were mixed by vortexing.

The batches were loaded onto columns filled with three layers of silica paper (diameter of the filter: 7.25 mm) and drawn through the silica membrane by the application of a vacuum (300 mbar reduction of pressure compared to normal pressure). When the solution had completely run through, as the first part of a threefold analysis each solution was washed with 2 mL of washing solution as per WO 2005/111059 A2, then with 4 mL washing solution as per WO 2005/111059 A2. As alternatives in the threefold analysis each solution was washed with 2 mL of the endotoxin removal buffer and then with 4 mL of alcoholic washing buffer. The washing steps were all carried out under a vacuum pressure of 0.3 bar in comparison to normal pressure.

All six batches were freed of ethanol residue by centrifugation at 11,000×g for 1 min. Elution was achieved by the addition of 500 µL H2O to each and centrifugation at 11,000×g for 1 min.

The eluted DNA was measured photometrically (spectrum from 200 nm to 300 nm) and the endotoxin content measured by means of the chromogenic LAL-Test (Pyrochrome, 260260PA-25, Pyroquant Diagnostik Ltd.). A control standard endotoxin (EC010-5, Pyroquant Diagnostik Ltd.) was used as quantification standard. For the measurement, the eluate was diluted 1:1,000 with water.

Result of Comparative Test 1

This example shows that the washing solutions known from WO 2005/111059 A2 require special conditions, for example a larger filter area or the presence of detergent in the binding buffer. These requirements lead to increased complexity, which can be considered a disadvantage in sequential processing.

Result of Comparative Test 2

Figure 1:
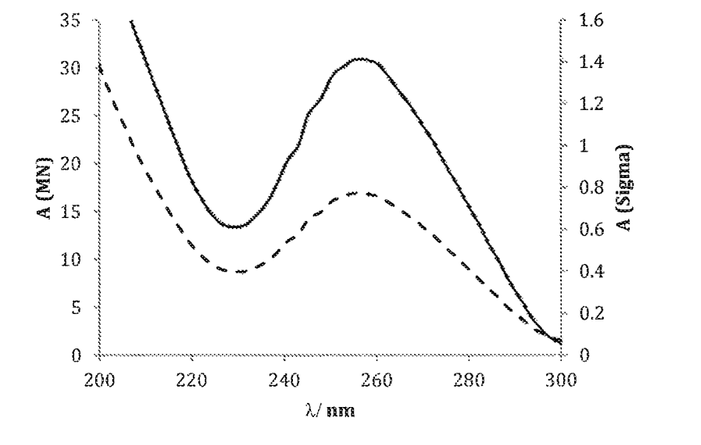
FIG. 1 shows results of the process according to the invention as a continuous line and the process according to WO 2005/111059 as a dashed line.

The photometric measurement as per FIG. 1 gave the following results:

| Invent$^n$ | Compar$^n$ | Invent$^n$ | Compar$^n$ | invent$^n$ | Compar$^n$ |
|---|---|---|---|---|---|
| µg DNA/eluate | | A260/A280 | | A260/A230 | |
| 454 | 12 | 1.86 | 1.76 | 2.28 | 1.89 |
| 452 | 12 | 1.86 | 1.78 | 2.28 | 1.93 |
| 431 | 9 | 1.86 | 1.77 | 2.29 | 1.89 |
| 446 | 11 | 1.86 | 1.77 | 2.28 | 1.90 |

In FIG. 1, the results according to the invention are shown as a continuous line and those of the process according to WO 2005/111059 A2 as a dashed line. It is apparent that the use of wash buffer 1 and wash buffer 2 from WO 2005/111059 A2 removed a majority of the DNA. The purity conditions indicate clean DNA in all cases (Soil: A260/A280=1.8 to 1.9, A260/A230=1.9 to 2.3).

LAL-Test:

| | EU/eluate | µg DNA/eluate | EU/µg |
|---|---|---|---|
| Invent$^n$ | 4796 | 454 | 11 |
| | 3965 | 452 | 9 |
| | 3178 | 431 | 7 |
| | 3980 | 446 | 9 |
| Comp$^n$ | 9840 | 12 | 795 |
| | 10207 | 12 | 823 |
| | 10259 | 9 | 1207 |
| | 10102 | 11 | 911 |

Although the DNA quantity in WO 2005/111059 A2 is markedly less (approx. 2.5% compared to the invention), the content of endotoxin is around 250% higher. It follows that a way has been found to separately precipitate DNA and endotoxins, and then remove the precipitated endotoxins using the solution described in this invention.

The invention claimed is:

1. A process for purifying nucleic acids from a biologic sample containing nucleic acid, comprising the following steps:
   a) preparing a fluid sample containing nucleic acid and endotoxin each in dissolved form;
   b) precipitating at least the nucleic acid and endotoxin from the fluid sample onto the surface of a solid carrier material selected from the group consisting of mineral carrier materials, quartz fibers, silica, glass, aluminum oxide, zeolite, titanium dioxide, zirconium dioxide, and combinations thereof;

c) washing the precipitated constituents of the liquid sample from step b) to at least partially remove the endotoxin with a washing solution which contains
(i) an amine compound of formula (I), (I)

wherein $R^1$, $R^2$ and $R^3$ independently of each other stand for a hydrogen atom, a ($C_1$ to $C_6$)-alkyl group, a ($C_1$ to $C_6$)-monohydroxyalkyl group, a ($C_2$ to $C_6$)-dihydroxyalkyl group, a ($C_3$ to $C_6$)-trihydroxyalkyl group, and at least one of the residues $R^1$, $R^2$ and $R^3$ differs from a hydrogen atom and with a molar mass of ≤500 g/mol and;
(ii) a $C_1$-$C_6$-monoalcohol, isopropanol, or a combination thereof, and
having a pH-value (20° C.) in the range from pH 3.0 to pH 8.5; and
d) dissolving the remaining nucleic acid derived from the washed, precipitated constituents from step c) by means of a dissolving buffer and capturing the dissolved nucleic acids,
wherein
the washing solution of step c) comprises the amine compound in a concentration of 200 mmol/L to 1,000 mmol/L.

2. The process according to claim 1, wherein in step b) at least nucleic acid and endotoxin are precipitated by adsorption or precipitation.

3. The process according to claim 1, wherein in step b) at least nucleic acid and endotoxin are separated as solids by precipitation, comprising
i) collecting the precipitated nucleic acid and entotoxin on the surface of a solid carrier material, or
ii) compacting the precipitated nucleic acid and entotoxin by centrifugation.

4. The process according to claim 1, wherein the amine compound is selected from the group consisting of triethylamine, triethanolamine, 2-amino-2-(hydroxymethyl)-propane-1,3-diol, 2,2-bis(hydroxy-methyl)-2,2',2"-nitrilotriethanol, 1,3-bis[tris(hydroxymethyl)methylamino]propane, and mixtures thereof.

5. The process according to claim 1, wherein the washing solution of step c) contains the amine compound in a concentration of 200 mmol/L to 800 mmol/L.

6. The process according to claim 1, wherein the nitrogen atom of the amino group in the amine compound is at least 50% protonated.

7. The process according to claim 1, wherein the washing solution contains the $C_1$-$C_6$-monoalcohol in a total concentration of 20 to 80% by weight relative to the total weight of the washing solution.

8. The process according to claim 1, wherein the washing solution of step c) has a pH-value (20° C.) in the range from pH 3.0 to 7.5.

9. The process according to claim 1 wherein at least 50% by weight of the endotoxin of the fluid sample are removed in the process removed.

10. A method of claim 1 comprising utilizing a washing solution comprising
(i) an amine compound of formula (I), (I)

wherein $R^1$, $R^2$ and $R^3$ independently of each other stand for a hydrogen atom, a ($C_1$ to $C_6$)-alkyl group, a ($C_1$ to $C_6$)-monohydroxyalkyl group, a ($C_2$ to $C_6$)-dihydroxyalkyl group, a ($C_3$ to $C_6$)-trihydroxyalkyl group, and at least one of the residues $R^1$, $R^2$ and $R^3$ differs from a hydrogen atom and with a molar mass of ≤500 g/mol and
(ii) a $C_1$-$C_6$-monoalcohol, isopropanol, or a combination thereof having a pH-value (20° C.) in the range from pH 3.0 to pH 8.5,
to at least partially remove endotoxin from a nucleic acid-containing sample wherein the washing solution comprises the at least one amine compound in a concentration of 200 mmol/L to 1,000 mmol/L.

11. The method according to claim 10 wherein the nucleic acid and the endotoxin are bound to the surface of a solid carrier material.

12. A kit for purifying nucleic acids comprising a washing solution, which contains
(i) an amine compound of formula (I), (I)

wherein $R^1$, $R^2$ and $R^3$ independently of each other stand for a hydrogen atom, a ($C_1$ to $C_6$)-alkyl group, a ($C_1$ to $C_6$)-monohydroxyalkyl group, a ($C_2$ to $C_6$)-dihydroxyalkyl group, a ($C_3$ to $C_6$)-trihydroxyalkyl group, and at least one of the residues $R^1$, $R^2$ and $R^3$ differs from a hydrogen atom and with a molar mass of ≤500 g/mol and
(ii) a $C_1$-$C_6$-monoalcohol, isopropanol, or a combination thereof and
having a pH-value (20° C.) in the range from pH 3.0 to pH 8.5,
and an additional constituent selected from the group consisting of an instruction manual to perform the process according to claim 1, a binding buffer, and a dissolving buffer, wherein the washing solution contains the amine compound in a concentration of 200 mmol/L to 1,000 mmol/L.

* * * * *